United States Patent [19]

Zschocke et al.

[11] 4,028,399
[45] June 7, 1977

[54] CARBAMATE

[75] Inventors: Albrecht Zschocke, Bad Durkheim;
Horst Kummer, Ludwigshafen;
Heinrich Adolphi, Limburgerhof, all
of Germany

[73] Assignee: Badische Anilin- & Soda-Fabrik Aktiengesellschaft, Ludwigshafen (Rhine), Germany

[22] Filed: Feb. 17, 1976

[21] Appl. No.: 658,408

Related U.S. Application Data

[63] Continuation of Ser. No. 500,150, Aug. 23, 1974, abandoned, which is a continuation-in-part of Ser. No. 26,747, April 8, 1970, abandoned.

[30] Foreign Application Priority Data

Apr. 18, 1969 Germany .......................... 1919747

[52] U.S. Cl. .......................... 260/479 C; 424/311
[51] Int. Cl.$^2$ ...................................... C07C 125/06
[58] Field of Search ................................ 260/479 C

[56] References Cited

UNITED STATES PATENTS 3,422,198  1/1969  Brooker et al. ................ 260/479 C

OTHER PUBLICATIONS

Metcalf et al., J. Arg. Food Chem., vol. 13, No. 3, pp. 224–226 (1965).

*Primary Examiner*—Jane S. Myers
*Attorney, Agent, or Firm*—Keil, Thompson & Shurtleff

[57] ABSTRACT

3,5-diethylphenyl-N-methylcarbamate, which has a good insecticidal action, and a process for controlling insects with this compound.

1 Claim, No Drawings

CARBAMATE

This is a continuation, of application Ser. No. 500,150 filed Aug. 23, 1974, now abandoned, which application is a continuation-in-part of application Ser. No. 26,747 which was filed in the Patent Office on Apr. 8, 1970, now abandoned.

The present invention relates to the new carbamic acid ester 3,5-diethyl-phenyl-N-methylcarbamate and insecticides containing this active ingredient.

It is known to use substituted phenyl-N-methylcarbamates, e.g. 4-dimethyl-amino-3,5-dimethyl-N-methylcarbamate, 3-isopropyl-5-methyl-N-methylcarbamate and 3,4-dimethyl-6-chloro-N-methylcarbamate, as insecticidal active ingredients; however, their action is not satisfactory.

We have now found that the new compound 3,5-diethyl-phenyl-N-methylcarbamate having the formula

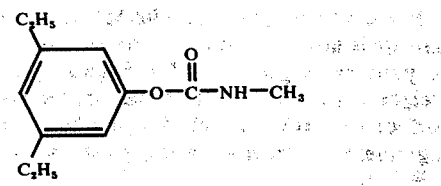

has an extremely strong insecticidal action.

It is possible to treat the insects direct with the active ingredient or the places where the insects are found. Examples of such places are houses, offices, stables, storerooms, cellars and barns. The active ingredient may also be applied to animals, e.g. cattle and sheep, to kill the insects infesting the animals.

The following details illustrate the preparation of the new active ingredient.

7.5 parts (by weight) of 3,5-diethylphenol [Ber. 32, 2392 (1899)] is dissolved in 20 parts of acetone to which 4 drops of triethylamine have been added, and a solution of 3.15 parts of methyl isocyanate in 20 parts of acetone is added to the resultant mixture. The mixture is kept for several hours at room temperature and then cooled to $-25°$ C. The precipitate formed is suction filtered and dried. 9 parts of 3,5-diethylphenyl-N-methylcarbamate having a melting point of 93° C is obtained.

The agent according to the invention may be used as a solution, emulsion, suspension or dust. The form of application depends entirely on the purpose for which the agent is being used; in any case it should ensure a fine distribution of the active ingredient.

For the preparation of solutions to be sprayed direct, the solution in water is suitable. However, hydrocarbons having boiling points higher than 150° C, e.g. tetrahydronaphthalene or alkylated naphthalenes, or organic liquids having boiling points higher than 150° C and having one or more than one functional group e.g. the keto group, the ether group, the ester group or the amide group, this group or these groups being attached as substituent(s) to a hydrocarbon chain or being a component of a heterocyclic ring, may also be used as spray liquids.

Aqueous formulations may be prepared from emulsion concentrates, pastes or wettable powders by adding water. To prepare emulsions the ingredient as such or dissolved in a solvent may be homogenized in water or organic solvents by means of wetting or dispersing agents, e.g. polyethylene oxide adducts. Concentrates which are suitable for dilution with water may be prepared from active ingredient, emulsifying or dispersing agent and possibly solvent.

Dusts may be prepared by mixing or grinding, the active ingredient with a solid carrier, e.g. kieselguhr, talc, clay or fertilizers.

The following Examples demonstrate the action of the agent according to the invention. By way of comparison, the following known active ingredients are used:

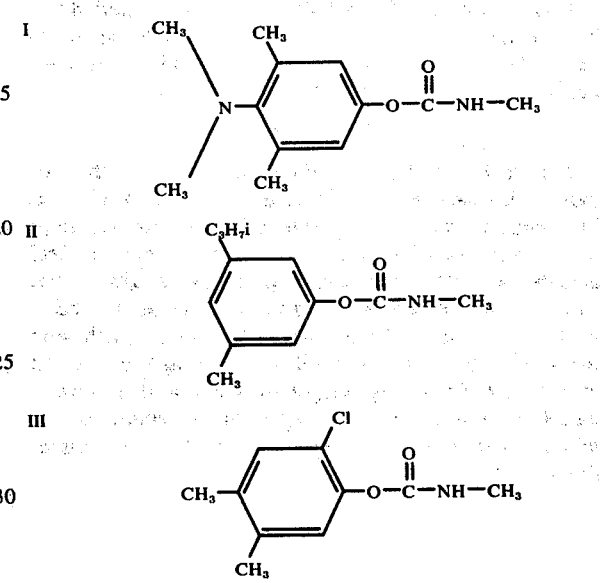

EXAMPLE 1

ADMINISTRATION TEST WITH COMMON HOUSEFLIES 1 mm³ of the acetonic solution of the active ingredients is administered to the ventral abdomen of houseflies under $CO_2$ narcosis. The kill rate on the insects thus treated is determined after 4 hours, from which the mortality curve is calculated. $1 = 1.10^{-6}$ g.

| RESULTS | | |
|---|---|---|
| Active ingredient according to the invention | $LD_{50}$ | 0.12 /fly |
| Comparative substance I | $LD_{50}$ | 1.2 /fly |
| Comparative substance II | $LD_{50}$ | 0.26 /fly |
| Comparative substance III | $LD_{50}$ | 10.0 /fly |

EXAMPLE 2

BREEDING TEST WITH DROSOPHILA MELANOGASTER

Emulsions of the active ingredients are each mixed with 40 g of a bran culture medium. Drosophila are allowed to lay eggs on the culture mediums, and the development on each medium is judged after 10 days.

| RESULTS | |
|---|---|
| Active ingredient according to the invention | 2.5 ppm growth inhibition |
| Comparative substance I | 12.5 ppm growth inhibition |
| Comparative substance II | 50.0 ppm growth inhibition |

| -continued | |
|---|---|
| RESULTS | |
| Comparative substance III | 6.25 ppm growth inhibition |

These Examples demonstrate the superiority of the active ingredient according to the invention over known active ingredients.

EXAMPLE 3

70 parts by weight of 3,5-diethylphenyl-N-methylcarbamate is mixed with 30 parts by weight of N-methyl-α-pyrrolidone. A mixture is obtained which is suitable for application in the form of very fine drops.

EXAMPLE 4

20 parts by weight of 3,5-diethylphenyl-N-methylcarbamate is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 5

20 parts by weight of 3,5-diethylphenyl-N-methylcarbamate is well mixed with 3 parts by weight of the sodium salt of diisobutylnaphthalene-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 6

3 parts by weight of 3,5-diethylphenyl-N-methylcarbamate is intimately mixed with 97 parts by weight of particulate kaolin. A dust is obtained containing 3% by weight of the active ingredient.

EXAMPLE 7

30 parts by weight of 3,5-diethylphenyl-N-methylcarbamate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:
1. 3,5-diethylphenyl-N-methylcarbamate.

* * * * *